(12) United States Patent
Overholser et al.

(10) Patent No.: US 9,011,846 B2
(45) Date of Patent: Apr. 21, 2015

(54) THROMBIN ISOLATED FROM BLOOD AND BLOOD FRACTIONS

(75) Inventors: Hillary Overholser, Goshen, IN (US); Jennifer Woodell-May, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 537 days.

(21) Appl. No.: 13/099,087

(22) Filed: May 2, 2011

(65) Prior Publication Data

US 2012/0282240 A1 Nov. 8, 2012

(51) Int. Cl.
*A61K 38/48* (2006.01)
*A61L 24/10* (2006.01)
*A61K 35/14* (2006.01)
*A61L 24/00* (2006.01)

(52) U.S. Cl.
CPC ............... *A61L 24/108* (2013.01); *A61K 35/14* (2013.01); *A61L 24/0005* (2013.01); *A61K 38/4833* (2013.01)

(58) Field of Classification Search
None
See application file for complete search history.

(56) References Cited

U.S. PATENT DOCUMENTS

| | | | |
|---|---|---|---|
| 4,152,270 A | 5/1979 | Cornell | |
| 4,411,794 A | 10/1983 | Schwinn et al. | |
| 4,853,137 A | 8/1989 | Ersson | |
| 5,480,378 A | 1/1996 | Weis-Fogh et al. | |
| 5,560,830 A | 10/1996 | Coleman et al. | |
| 5,571,418 A | 11/1996 | Lee et al. | |
| 5,585,007 A | 12/1996 | Antanavich et al. | |
| 5,707,331 A | 1/1998 | Wells et al. | |
| 5,733,545 A | 3/1998 | Hood, III | |
| 5,788,662 A | 8/1998 | Antanavich et al. | |
| 5,830,359 A | 11/1998 | Knight et al. | |
| 5,985,315 A | 11/1999 | Patat et al. | |
| 6,007,811 A | 12/1999 | Sawyer et al. | |
| 6,027,655 A | 2/2000 | Holm | |
| 6,063,297 A | 5/2000 | Antanavich et al. | |
| 6,214,338 B1 | 4/2001 | Antanavich et al. | |
| 6,287,558 B1 | 9/2001 | Lanza et al. | |
| 6,398,972 B1 | 6/2002 | Blasetti et al. | |
| 6,524,568 B2 | 2/2003 | Worden | |
| 6,623,472 B1 | 9/2003 | Reincke et al. | |
| 6,713,246 B1 | 3/2004 | Reinecke et al. | |
| 6,759,188 B2 | 7/2004 | Reinecke et al. | |
| 6,790,371 B2 | 9/2004 | Dolecek | |
| 6,830,762 B2 | 12/2004 | Baugh et al. | |
| 6,899,813 B2 | 5/2005 | Dolecek et al. | |
| 6,905,612 B2 | 6/2005 | Dorian et al. | |
| 7,011,852 B2 | 3/2006 | Sukavaneshvar et al. | |
| 7,112,342 B2 | 9/2006 | Worden | |
| 7,179,391 B2 | 2/2007 | Leach et al. | |
| 7,223,346 B2 | 5/2007 | Dorian et al. | |
| 7,374,678 B2 | 5/2008 | Leach et al. | |
| 7,411,006 B2 | 8/2008 | Shanbrom | |
| 7,465,293 B2 | 12/2008 | Reinecke et al. | |
| 7,470,371 B2 | 12/2008 | Dorian et al. | |
| 7,553,413 B2 | 6/2009 | Dorian et al. | |
| 7,694,828 B2 | 4/2010 | Swift et al. | |
| 7,708,152 B2 | 5/2010 | Dorian et al. | |
| 7,901,344 B2 | 3/2011 | Yoo | |
| 7,914,689 B2 | 3/2011 | Higgins et al. | |
| 8,048,321 B2 | 11/2011 | Leach et al. | |
| 2001/0009757 A1 | 7/2001 | Bischof et al. | |
| 2003/0138910 A1 | 7/2003 | Reinecke et al. | |
| 2003/0198687 A1 | 10/2003 | Bennett et al. | |
| 2003/0205538 A1 | 11/2003 | Dorian et al. | |
| 2004/0120942 A1 | 6/2004 | McGinnis et al. | |
| 2004/0182788 A1 | 9/2004 | Dorian et al. | |
| 2004/0182795 A1 | 9/2004 | Dorian et al. | |
| 2004/0251217 A1 | 12/2004 | Leach et al. | |
| 2005/0084962 A1 | 4/2005 | Simon | |
| 2005/0109716 A1 | 5/2005 | Leach et al. | |
| 2005/0130301 A1 | 6/2005 | McKay et al. | |
| 2005/0186120 A1 | 8/2005 | Dorian et al. | |
| 2005/0196393 A1 | 9/2005 | Shanbrom | |
| 2005/0196874 A1 | 9/2005 | Dorian et al. | |
| 2006/0051865 A1 | 3/2006 | Higgins et al. | |
| 2006/0057693 A1 | 3/2006 | Simon | |
| 2006/0140923 A1 | 6/2006 | Evangelista et al. | |
| 2006/0175244 A1 | 8/2006 | Dorian et al. | |
| 2006/0178610 A1 | 8/2006 | Nowakowski | |

(Continued)

FOREIGN PATENT DOCUMENTS

EP 0237981 A2 9/1987
JP 2004/269409 A 9/2004

(Continued)

OTHER PUBLICATIONS

Kumar et al., J Extra Corpor. Technol. (JECT), 2008, vol. 40, No. 2, p. 94-98.*

(Continued)

*Primary Examiner* — Kade Ariani
(74) *Attorney, Agent, or Firm* — Harness, Dickey (57) ABSTRACT

Methods, apparatus, and compositions related to generating and using thrombin. Methods include preparing a solution comprising thrombin by precipitating fibrinogen from a liquid comprising whole blood or a blood fraction. Precipitated fibrinogen is removed from the liquid to form a post-precipitation liquid that is incubated with calcium and a plurality of beads to form a clot. A solution comprising thrombin is separated from the clot. Thrombin prepared thereby can be used as a tissue sealant and in methods of applying a tissue sealant to subject, including application of an autologous tissue sealant.

23 Claims, 6 Drawing Sheets

(56) References Cited

U.S. PATENT DOCUMENTS

| | | |
|---|---|---|
| 2007/0075016 A1 | 4/2007 | Leach |
| 2007/0207161 A1 | 9/2007 | Ralph |
| 2007/0208321 A1 | 9/2007 | Leach et al. |
| 2008/0011684 A1 | 1/2008 | Dorian et al. |
| 2008/0044852 A1* | 2/2008 | Kanayinkal et al. ......... 435/68.1 |
| 2008/0064626 A1 | 3/2008 | Zanella |
| 2008/1093424 | 8/2008 | McKale et al. |
| 2008/0217263 A1 | 9/2008 | Higgins et al. |
| 2008/0306431 A1 | 12/2008 | Yoo |
| 2009/0018313 A1 | 1/2009 | Shanbrom |
| 2009/0047242 A1 | 2/2009 | Reinecke et al. |
| 2009/0101599 A1 | 4/2009 | Dorian et al. |
| 2009/0112146 A1 | 4/2009 | Wratten et al. |
| 2009/0181019 A1 | 7/2009 | Solinger |
| 2009/0236297 A1 | 9/2009 | Dorian et al. |
| 2009/0317439 A1 | 12/2009 | Turzi et al. |
| 2010/0008992 A1 | 1/2010 | Ichim |
| 2010/0015129 A1 | 1/2010 | Abramson et al. |
| 2010/0055087 A1 | 3/2010 | Higgins et al. |
| 2010/0125236 A1 | 5/2010 | Bare et al. |
| 2010/0140182 A1 | 6/2010 | Chapman et al. |
| 2010/0226909 A1 | 9/2010 | Hecker et al. |
| 2010/0256595 A1 | 10/2010 | Leach et al. |
| 2011/0020196 A1 | 1/2011 | Grippi et al. |
| 2011/0059082 A1 | 3/2011 | Germer et al. |
| 2011/0059084 A1 | 3/2011 | Osterroth et al. |
| 2011/0189172 A1 | 8/2011 | Solinger et al. |
| 2011/0268708 A1 | 11/2011 | Lin et al. |
| 2012/0027746 A1 | 2/2012 | Dorian et al. |
| 2012/0093936 A1 | 4/2012 | Lindenberg et al. |

FOREIGN PATENT DOCUMENTS

| | | |
|---|---|---|
| WO | 99/23111 A1 | 5/1999 |
| WO | 00/74713 A1 | 12/2000 |
| WO | 2004/050904 A1 | 6/2004 |
| WO | 2007/127834 A2 | 11/2007 |
| WO | 2008/100442 A1 | 8/2008 |
| WO | 2009/108890 A1 | 9/2009 |
| WO | 2011/031553 A2 | 3/2011 |
| WO | 2012/030593 A2 | 3/2012 |

OTHER PUBLICATIONS

NPL serach results, 2013.*
Bielecki, Antibacterial effect of autologous platelet gel enriched with growth factors and other active substances, Journal of Bone & Joint Surgery 89-B(3), 417-420 (2007).
Biomet Biologics, Inc., Plasmax Plasma Concentrate Brochure, 6 pages (2006).
Burnoff, Blood-Derived, Tissue Engineering Biomaterials, HPPS, Biomedical Engineering-Applications, Basis & Communications, 16:6, 294-304 (Dec. 2004).
Cell Factor Technologies, Inc. "GPS® Platelet Concentrate System" Product Brochure (9 pages) 2004.
Cell Factor Technologies, Inc. "Gravitational Platelet Separation System" User Manual (2005) 13 pages.
Dallari, et al. "Enhanced Tibial Osteotomy Healing with Use of Bone Grafts Supplemented with Platelet Gel or Platelet Gel and Bone Marrow Stromal Cells," The Journal of Bone and Jooint Surgery, 2413-2420 (2007).
DePalma, L. et al., "The Preparation of Fibrinogen Concentrate for Use as Fibrin Glue by Four Different Methods," Transfusion: vol. 33, pp. 717-720 (1993).
Floryan, Intraoperative use of autologous platelet-rich and platelet-poor plasma, Home Study Program, AORN Journal, 80:4, 667-674 (Oct. 2004).
Hood et al., Poster Location 8—Autologous Platelet Gel, An Effective, Convenient, Bioactive Wound Sealant, p. 67, 2014.
Hood, A. et al. "Perioperative Autologous Sequestration III: A New Physiologic Clue with Wound Healing Properties", Proceedings of the American Academy of Cardiovascular Perfusion, vol. 14, pp. 126-129 (Jan. 1993).
Kumar, Vijay et al. "Stability of Human Thrombin Produced From 11 ml of Plasma Using the Thrombin Processing Device," Journal of American Society of Extra-Corporeal Technology. JECT: Mar. 2005:37; 390-395.
Kumar, Vijay et al. "Whole Blood Thrombin: Development of a Process for Intra-Operative Production of Human Thrombin." Journal of American Society of Extra-Corporeal Technology. JECT: Apr. 2007; 39:18-23.
Kumar, Vijay et al., "Autologous Thrombin: Intraoperative Production From Whole Blood." Journal of American Society of Extra-Corporeal Technology. JECT: Apr. 2008; 40:94-98.
Lau, H., "Fibrin Sealant Versus Mechanical Stapling for Mesh Fixation During Endoscopic Extraperitoneal Inguinal Hernioplasty, A Randomized Prospective Trial," Annals of Surgery, 242:5, pp. 670-675 (2005).
Lee, M. et al., "Applications of Fibrin Sealant in Surgery," Surg Innov., 12:3, Abstract only, 1 page (2005).
Li MinKang et al. "Combination of Extracting Main Functional Proteins such as Thrombin and Immunoglobulin from Pig Plasma" Journal of the Graduate School of the Chinese Academy of Sciences, vol. 24 No. 3 pp. 357-360 (May 15, 2007).
Li Minkang et al. "Separation and Purifications of Thrombin from Pig Plasma" Journal of Shananxi University of Science and Technology vol. 21 pp. 40-42 (Aug. 25, 2003).
Meijer, H. et al. "The Production of Anti-Inflammatory Cytokines in whole Blood by physico-chemical induction" Inflamm. Res., vol. 52 (pp. 404-407) Oct. 2003.
Morizaki et al., "The Effects of Platelet-Rich Plasma on Bone Marrow Stromal Cell Transplants for Tendon Healing in Vitro," J Hand Surg Am; 35(11): 1833-1841 (Nov. 2010).
Oz et al., "Autologous fibrin glue from intraoperatively collected platelet-rich plasma," Ann Thorac Surg; 53:530-531 (1992).
Schmidt, S. C. et al. "Autologous Fibring Sealant (Vivostat) for Mesh Fixation in Laparoscopic Transabdominal Preperitoneal Hernia Repair," Endoscopy, 38:8, pp. 841-844 (2006).
Semple, Elizabeth, PhD, et al. "Quality of Thrombin Produced From the Patient's Own Plasma Using the TPD™, a New Thrombin-Processing Device." Journal of American Society of Extra-Corporeal Technology. JECT: 2005; 37:196-200.
Weisman, R. et al. "Biochemical Characterization of Autologous Fibrinogen Adhesive" Laryngoscope, vol. 97, pp. 1186-1190 (Oct. 1987).
Yang, T. et al. "Recent Applications of Polyacrylamide as Biomaterials" Recent Patents on Materials Science, vol. 1, pp. 29-40 (2008).
Zieren, J. et al. "Effects of Fibrin Glue and Growth Factors Released from Platelets on Abdominal Hernia Repair with a Resorbable PGA Mesh: Experimental Study" Journal of Surgical Research, 85:2, Abstract Only, 2 pages (Aug. 1999).

* cited by examiner

THROMBIN ISOLATED FROM BLOOD AND BLOOD FRACTIONS

The present technology relates to methods for isolating thrombin from blood and blood fractions, including compositions produced by such methods and methods of administering such compositions.

Whole blood, such as human whole blood, contains various proteins, cells, and other components. For example, whole blood can be separated into blood fractions such as platelet-rich plasma and platelet-poor plasma. Whole blood and plasma fractions include various clotting factors, such as thrombin, that can form a clot to heal a lesion or other opening in tissue or skin.

Thrombin is a multifunctional serine protease that can activate various clotting factors and can activate platelets. Thrombin can be generated from prothrombin by enzymatic cleavage of two sites on prothrombin by activated Factor X (Xa). Factor Xa activity is enhanced by binding to activated Factor V (Va), termed the prothrombinase complex. Once formed, thrombin-mediated proteolytic digestion of fibrinogen into fibrin monomer starts a reaction cascade that can lead to clot formation, which is typically the first step in wound healing. Thrombin can also function as a chemo-attractant to cells involved in wound healing and the resulting fibrin network has several functions including acting as a scaffold for collagen-producing fibroblasts, increasing phagocytosis, promoting angiogenesis, and binding growth factors that can further support the healing process. Platelets are also activated from the nonbinding to the binding mode. As a procoagulant, thrombin plays an important role in the arrest of bleeding; i.e., physiological hemostasis.

Rate of clot formation can be dependent on the concentration of thrombin and fibrinogen. Because of its important function in clot formation, thrombin can be utilized as a tissue sealant or glue and can be used in conjunction with fibrinogen. Applications for wound sealants comprising thrombin are numerous and include uses in skin grafting, neurosurgery, cardiac surgery, thoracic surgery, vascular surgery, oncologic surgery, plastic surgery, ophthalmologic surgery, orthopedic surgery, trauma surgery, head and neck surgery, gynecologic and urologic surgery, gastrointestinal surgery, dental surgery, drug delivery, tissue engineering, and dental cavity hemostasis, among others.

SUMMARY

The present technology includes methods, apparatus, and compositions that relate to isolating thrombin from blood and/or blood fractions, where the isolated thrombin can be used as an autologous clotting factor, for example.

Methods of preparing a solution comprising thrombin include precipitating fibrinogen from a liquid comprising whole blood or a blood fraction (e.g., platelet-poor plasma). Precipitated fibrinogen is removed from the liquid to form a post-precipitation liquid. Ways of removing precipitated fibrinogen include filtering the liquid or centrifuging the liquid to sediment precipitated fibrinogen. The post-precipitation liquid is then incubated with calcium and glass beads to form a clot and a solution comprising thrombin is separated from the clot.

Solutions and compositions comprising thrombin are provided that include thrombin prepared according to the present methods. These solutions and compositions can be included in methods of applying a tissue sealant to a site on a subject. For example, a solution comprising thrombin is prepared according to a method described herein. The thrombin is then applied to the site on the subject. In some cases, the thrombin is prepared using a liquid comprising whole blood or a blood fraction obtained from the subject, thereby providing thrombin autologous to the subject. Application of thrombin in applying a tissue sealant can further include the application of fibrinogen and calcium to the site on the subject.

It should be noted that the figures set forth herein are intended to exemplify the general characteristics of materials and methods among those of the present technology, for the purpose of the description of certain embodiments. These figures may not precisely reflect the characteristics of any given embodiment, and are not necessarily intended to define or limit specific embodiments within the scope of this technology.

DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing there from. A non-limiting discussion of terms and phrases intended to aid understanding of the present technology is provided at the end of this Detailed Description.

The present technology relates to methods of isolating thrombin from whole blood and/or a blood fraction and compositions, such as tissue sealants, comprising thrombin produced using such methods. The present technology further provides methods of applying a tissue sealant including thrombin to a site on a subject. For example, the tissue sealant can include thrombin that is mixed with fibrinogen and applied to form a clot or fibrin glue. Thrombin can also be used to clot various blood components at a point of care, where blood components include purified fibrinogen, whole blood, platelet-rich plasma (PRP), platelet-poor plasma (PPP) or concentrates thereof, and combinations thereof. Thrombin converts fibrinogen to fibrin and forms a clot that can function as a sealant. The clot can be applied to seal an incision site following surgery or to seal a wound, for example, and can also facilitate healing at the site. In some cases, the thrombin can be autologous to the subject.

The present methods of isolating thrombin from blood and blood fractions can provide thrombin having improved thrombin enzymatic activity. Other methods that generate or isolate thrombin can result in a thrombin product having lower activity than desired. For example, some methods provide thrombin that can clot platelet-rich plasma but do not provide enough thrombin activity to clot other products, such as concentrated plasma or bone marrow aspirate. However, the present methods include two steps for thrombin generation—fibrinogen precipitation and clot formation/prothrombin conversion to thrombin—that result in a solution comprising thrombin that has enough activity to effectively clot such products.

Figure 1:
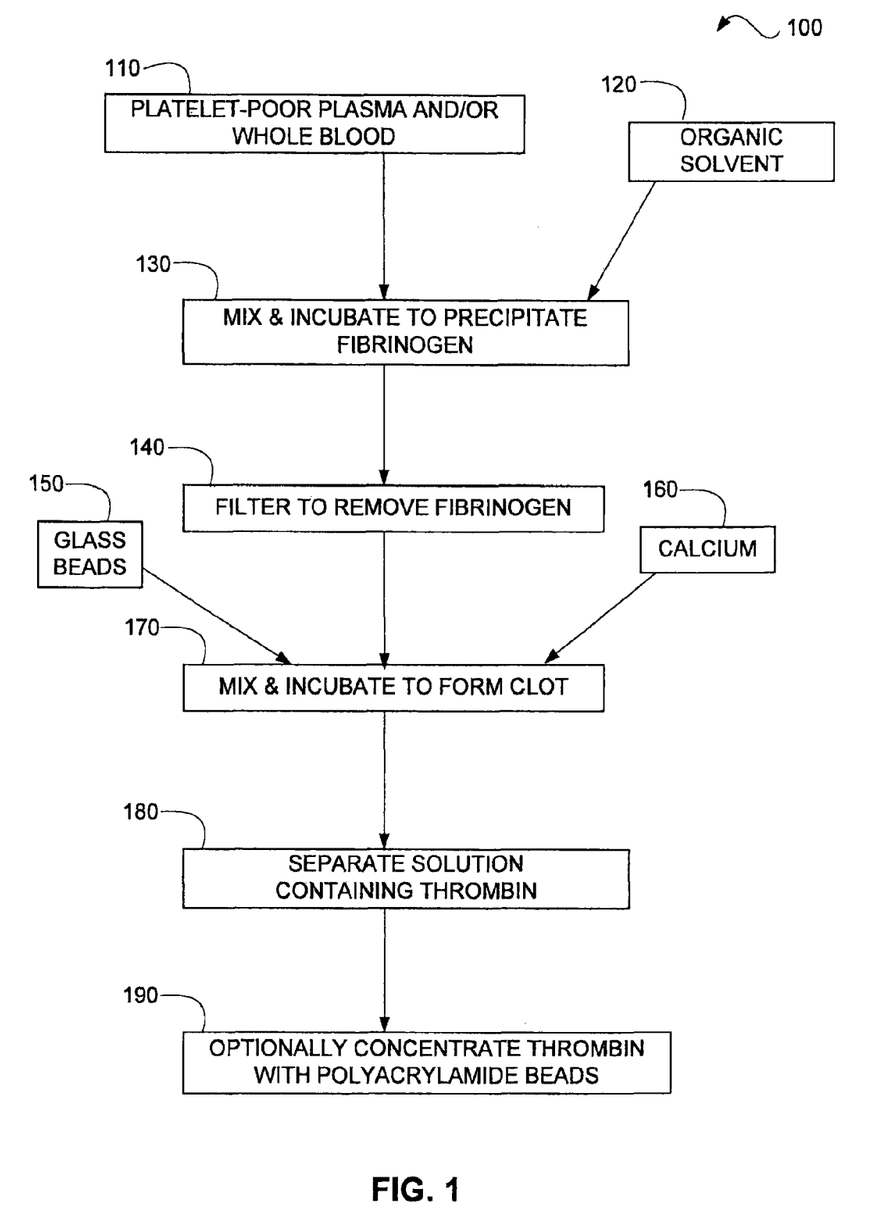
FIG. 1 is a diagrammatic illustration of a method of preparing a solution comprising thrombin according to the present technology.

With reference to FIG. 1, a method 100 for preparing a solution comprising thrombin is shown in diagrammatic fashion. Fibrinogen is precipitated from a liquid comprising whole blood and/or a blood fraction and the precipitated fibrinogen is removed to form a post-precipitation liquid. For example, whole blood and/or a blood fraction 110 are combined with organic solvent 120 to precipitate fibrinogen, as shown at 130. Precipitation of fibrinogen can include mixing the whole blood and/or a blood fraction 110 and the organic solvent 120 and further incubating for a period of time, such as about 10 minutes to about 20 minutes.

The liquid 110 may comprise whole blood. When whole blood is employed in the method 100, the whole blood can be combined with an anticoagulant. An example of a suitable anticoagulant includes Acid Citrate Dextrose (ACD), which is a solution of citric acid, sodium citrate, and dextrose in water that can be used to preserve blood. In some embodiments, the blood component may include ACD-A, which includes per 1000 ml: total citrate (as citric acid, anhydrous ($C_6H_8O_7$)) about 20.59 g to 22.75 g, dextrose ($C_6H_{12}O_6 * H_2O$) about 23.28 g to 25.73 g, and sodium (Na) about 4.90 g to 5.42 g. In some embodiments, ACD-B is used, which includes per 1000 ml: total citrate (as citric acid, anhydrous ($C_6H_8O_7$)) about 12.37 g to 13.67 g, dextrose ($C_6H_{12}O_6 * H_2O$) about 13.96 g to 15.44 g, and sodium (Na) about 2.94 g to 3.25 g. In some embodiments, whole blood can be anticoagulated with about a $1/10^{th}$ volume to about a $1/7^{th}$ volume of ACD-A. Other suitable anticoagulants include those known in the art, such as heparin, citrate phosphate dextrose (CPD), and ethylenediaminetetraacetic acid (EDTA). The anticoagulant may be placed in a syringe used for drawing blood from a subject, or it may be mixed with blood after the blood is drawn. The anticoagulant typically includes a chelating agent (e.g., citrate, EDTA) to complex free calcium ions.

Figure 4:
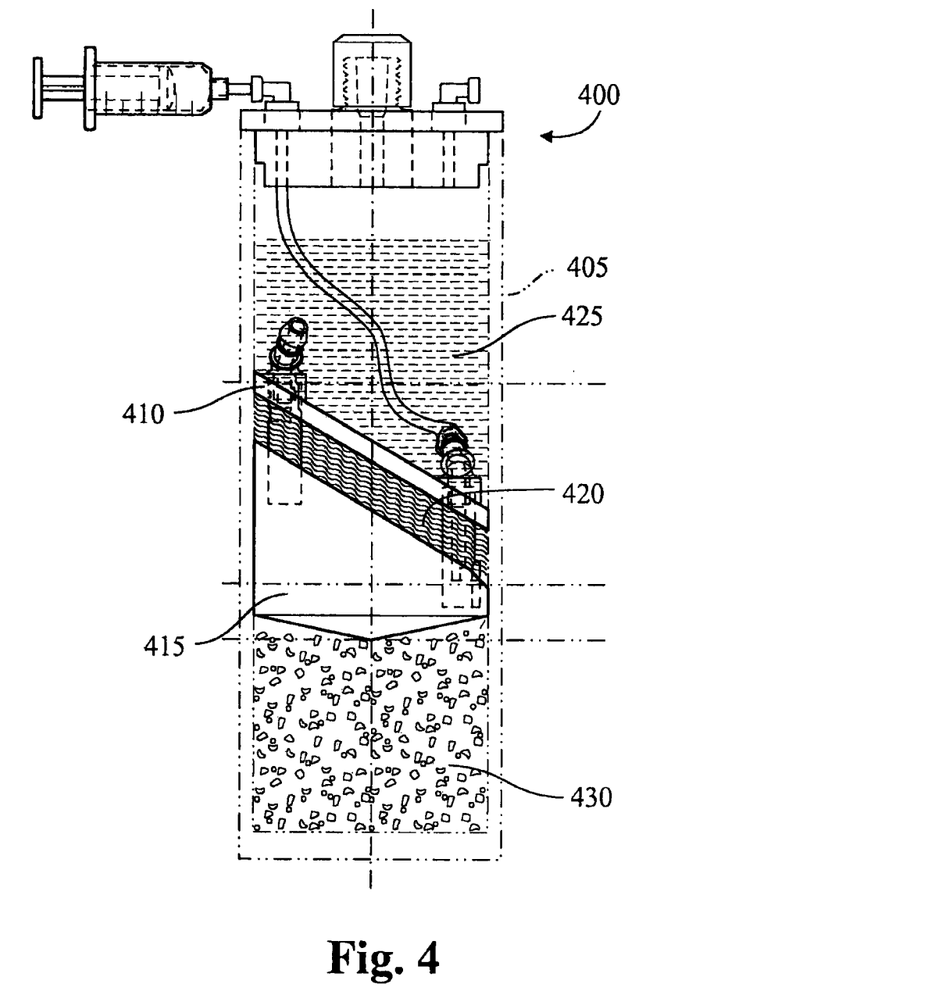
FIG. 4 is a partial cross-sectional view of a representative device for isolating a blood fraction according to methods of the present technology.

In some embodiments, the liquid 110 is a blood fraction. Suitable blood fractions 110 include platelet-poor plasma. Blood fraction 110 may be obtained by any of a variety of suitable methods, including those known in the art. One example of a device that may be used to prepare a blood fraction 110 is shown in FIG. 4. In this regard, the device 400 includes a container 405, such as a tube, that is placed in a centrifuge after being filled with blood. The container 405 includes a buoy system having an isolator 410 and a buoy 415. The buoy 415 has a selected density which is tuned to reach a selected equilibrium position upon centrifugation; this position lies between a more dense blood fraction and a less dense blood fraction. During centrifugation, the buoy 415 separates the blood within the container 405 into at least two fractions, without substantially commingling the fractions, by sedimenting to a position between the two fractions. In this regard, the isolator 410 and the buoy 415 define a layer comprising platelet-rich plasma 420, while less dense platelet-poor plasma 425 generally fractionates above the isolator 410, and more dense red blood cells 430 generally fractionate below the buoy 415.

Following centrifugation of the device 400, a syringe or tube may be interconnected with a portion of the buoy system to extract the blood fraction (e.g., platelet-rich plasma and/or the platelet-poor plasma). Commercially available embodiments of such devices include the GPS® II Platelet Concentrate System, from Biomet Biologics, LLC (Warsaw, Ind., USA) and the GPS® III Platelet Separation System, from Biomet Biologics, LLC (Warsaw, Ind., USA).

Devices that may be used to isolate a blood fraction for use at 110 in FIG. 1 further include those described, for example, in U.S. Pat. No. 6,398,972, Blasetti et al., issued Jun. 4, 2002; U.S. Pat. No. 6,649,072, Brandt et al., issued Nov. 18, 2003; U.S. Pat. No. 6,790,371, Dolocek, issued Sep. 14, 2004; U.S. Pat. No. 7,011,852, Sukavaneshvar et al., issued Mar. 14, 2006; U.S. Pat. No. 7,179,391, Leach et al., issued Feb. 20, 2007 (incorporated by reference herein); U.S. Pat. No. 7,374,678, Leach et al., issued May 20, 2008 (incorporated by reference herein); U.S. Pat. No. 7,223,346, Dorian et al., issued May 29, 2007 (incorporated by reference herein); and U.S. Pat. No. 7,708,152, Dorian et al., issued May 4, 2010 (incorporated by reference herein).

Other methods may be used to isolate the blood fraction 110. For example, whole blood can be centrifuged without using a buoy system, whole blood may be centrifuged in multiple stages, continuous-flow centrifugation can be used, and filtration can also be used. In addition, a blood fraction can be produced by separating plasma from red blood cells using a slow speed centrifugation step to prevent pelleting of the platelets. In other embodiments, a buffy coat fraction formed from centrifuged blood can be separated from remaining plasma.

In addition, a variety of other commercially available devices may be used to isolate a blood fraction at 110, including the Magellan™ Autologous Platelet Separator System, commercially available from Medtronic, Inc. (Minneapolis, Minn.); SmartPReP™, commercially available from Harvest Technologies Corporation (Plymouth, Mass.); the Autolo-Gel™ Process, commercially available from Cytomedix, Inc. (Rockville, Md.); and the GenesisCS System, commercially available from EmCyte Corporation (Fort Myers, Fla.).

Returning to FIG. 1, as discussed above, the whole blood/blood fraction 110 is mixed with an organic solvent 120 in step 130. Suitable organic solvents 120 for precipitating fibrinogen in the whole blood and/or blood fraction 110 include water-miscible solvents such as alcohols (e.g., ethanol and methanol), and ketones (e.g., acetone). As the organic solvent is added, protein within the whole blood and/or blood fraction precipitates. In this manner, fibrinogen is precipitated from the whole blood and/or blood fraction. Without being limited by theory, the organic solvent may dehydrate protein surfaces, which may then associate by van der Waals forces, at least if they are isoelectric or reasonably close to it. Removal of water molecules from around charged groups can also de-shield them and allow charge interactions to occur more strongly. Salts can bind to protein surfaces making them less isoelectric and subsequently can interfere with organic solvent precipitation. Accordingly, precipitation using organic solvent may be carried out at low or reduced salt concentrations.

In practice, precipitation by adding an organic solvent can be carried out at room temperature (e.g., about 20-25° C.) or at lower temperatures. Examples of lower temperatures include about 4° C. down to about −20° C. Organic solvent can be slowly added and mixed with the whole blood and/or blood fraction. A test precipitation with a small amount of whole blood and/or blood fraction can be performed, taking out small samples following addition of various amounts of organic solvent, centrifuging, and assaying the supernatant in the samples to find out when fibrinogen is precipitated. The presence of precipitate can also be assayed to find out if and when protein is effectively being precipitated and whether fibrinogen in particular is precipitated, for example.

In various embodiments, the precipitation can include combining about 12 ml of platelet-poor plasma with about 7 ml of whole blood at room temperature. After centrifugation, the various supernatants and resuspended pellets can be assayed for protein content and can be subjected to protein electrophoresis in order to provide quantitative measurements of protein including fibrinogen.

Methods other than addition of organic solvent may be used to precipitate fibrinogen at 130. Examples include addition of polyvalent metal ions (e.g., $Ca^{2+}$, $Mg^{2+}$, $Mn^{2+}$, and $Fe^{2+}$), flocculation with polyelectrolytes (e.g., alginate, carboxymethycellulose, polyacrylic acid, tannic acid, and polyphosphates), non-ionic hydrophilic polymers (e.g., dextrans and polyalkylene glycols), isoelectric point precipitation by addition of acids (e.g., hydrochloric acid and sulfuric acid), and salting out by addition of a neutral salt (e.g., ammonium sulfate). Other suitable methods for precipitating proteins known in the art may be used to precipitate fibrinogen in the whole blood and/or blood fraction.

Step 130 can include incubating the whole blood and/or blood fraction liquid 110 with an organic solvent for a period of time suitable to precipitate protein including fibrinogen. Incubation may be at room temperature or at lower temperatures as described. Representative incubation times to precipitate fibrinogen include from about 10 minutes to about 20 minutes.

In some embodiments, the liquid comprising whole blood and/or blood fraction 110 includes platelet-poor plasma and the organic solvent 120 includes absolute ethanol (i.e., substantially 100% ethanol or 200 proof). Mixing and incubating to precipitate fibrinogen at 130 can include drawing the platelet-poor plasma into a syringe containing the ethanol. Examples of suitable volumes and ratios include about 12 ml of platelet-poor plasma and about 7 ml of 200-proof ethanol (or an equivalent). The platelet-poor plasma and ethanol are mixed and the syringe is incubated 10-20 minutes. The incubation may be at room temperature. The syringe can be fitted with a filter that will allow liquid to flow through but not precipitated fibrinogen.

In addition to or in lieu of the platelet-poor plasma, whole blood can be drawn into a syringe containing an anticoagulant, such as ACD-A, and ethanol. When an anticoagulant is combined with whole blood, the volume of organic solvent 120 (e.g., ethanol) used to precipitate fibrinogen can be changed to match the decreased amount of plasma in the whole blood. For example, 11 ml whole blood can be combined with 1 ml ACD-A and 2.2 ml ethanol.

Referring again to FIG. 1, following the precipitation at 130, the precipitated protein including fibrinogen is removed at 140 to provide a post-precipitation liquid. Removal of precipitated fibrinogen at 140 can include filtering the mixture using a filter that allows liquid to pass but retains precipitated proteins including fibrinogen. Alternatively, the precipitated protein including fibrinogen can be centrifuged to pellet or sediment the precipitated fibrinogen and the liquid supernatant collected as the post-precipitation liquid.

The post-precipitation liquid is then mixed and incubated with beads 150 and calcium 160 to form a clot, as shown at 170. The calcium may comprise a calcium salt, such as calcium chloride, calcium carbonate, calcium sulfate, and combinations thereof. The calcium may be provided in a solid form, such as salt crystals which may be premeasured to provide a particular concentration based on a particular container volume. Or, the calcium may be provided as a concentrated solution that is diluted by the post-precipitation liquid.

In some embodiments, the post-precipitation liquid may include a chelating agent, such as EDTA or citrate, which may be present due to the liquid comprising whole blood or a blood fraction in the precipitating step being treated with an anticoagulant. Calcium addition to a post-precipitation liquid that includes a chelating agent can be done in a manner that provides a final concentration of calcium greater than the amount of calcium that can be complexed by the chelating agent. In this case, the calcium addition provides uncomplexed calcium that can participate in the clotting cascade.

In some embodiments, the post-precipitation liquid is combined with the beads 150 and calcium 160 in a device as disclosed by U.S. Pat. No. 7,694,828, Swift et al., issued Apr. 13, 2010. An example of such a device is the Clotalyst™ Autologous Clotting Factor System, sold by Biomet Biologic, LLC (Warsaw, Ind.). For example, calcium chloride can be provided in the Clotalyst™ tube as a powder that is packaged in the tube with the beads or as a concentrated solution that comes with the Clotalyst™ Autologous Clotting Factor System and is added to the tube prior to use. The concentration of calcium upon mixing with a volume of post-precipitation liquid can be approximately $3.4 \times 10^{-4}$ M; this calcium concentration can reverse the effect of ACD-A used to anticoagulate the liquid comprising whole blood or a blood fraction in the precipitating step using the aforementioned volumes or ratios.

Beads 150 used at 170 to form the clot include activating beads such as glass beads. The beads can assist in activating a portion of the post-precipitation liquid to generate thrombin. Various beads include glass beads, polystyrene beads, or other appropriate beads. Polystyrene and/or glass beads 150 can activate various components of the post-precipitation liquid to produce thrombin and can assist in the separation and concentration of the clotting component. For example, glass beads or polystyrene beads may activate platelets present in the post-precipitation liquid. The beads may be any appropriate size, such as about 0.001 millimeters to about 3 millimeters. For example, glass beads may be provided in a tube, such as the Clotalyst™ device tube, which are about 2 millimeters in diameter.

In some embodiments, the mixture of post-precipitation liquid, beads, and calcium is agitated in forming the clot at 170. Agitation may be accomplished by inverting, shaking, rocking, stirring, or vortexing the tube or container holding the post-precipitation liquid, beads, and calcium. Agitation may be performed once, repeated multiple times, repeated periodically, or may be continuous. In some cases, a mixing assembly is used to agitate the post-precipitation liquid, beads, and calcium; e.g., as described by U.S. Pat. No. 7,694,828, Swift et al., issued Apr. 13, 2010.

The post-precipitation liquid, beads, and calcium can be kept in contact after or during mixing in order to form a clot at 170. For example, the mixture can be incubated for about 5 minutes to about 10 minutes to allow clot formation. Incubation may be at room temperature. In some embodiments, the mixture is incubated at a temperature above room temperature, such as 37° C., to promote clot formation.

As shown at 180 in FIG. 1, a solution comprising thrombin is separated from the clot formed in 170. The separating can include centrifuging the clot and removing a portion of the supernatant as the solution comprising thrombin. Centrifuging the clot can cause the beads, clot material, and any remaining cellular material to sediment and form a pellet so that a supernatant of a solution comprising thrombin can be decanted or withdrawn from the pellet. For example, centrifugation may be at about 3200 RPM for about 5 minutes.

Withdrawing the supernatant (i.e., the solution comprising thrombin) can be performed using a syringe, pipette, or other suitable means.

The solution comprising thrombin can optionally be concentrated, as shown at 190. Concentration can include use of a desiccating agent, such as desiccating polyacrylamide beads, which absorbs a portion of the liquid in the thrombin solution but can have a pore size that is too small for thrombin to enter the beads. The concentrated thrombin can then be separated from the liquid-filled polyacrylamide beads. Other methods can be used to concentrate and/or isolate the thrombin, including precipitation, filtration, lyophilization, and other methods known in the art.

The solution comprising thrombin may be used as-is or may be preserved for later use. For example, the thrombin solution may be preserved by adding glycerin, a polyol, or alcohol to the solution comprising thrombin; adding a chelator to complex calcium in the solution comprising thrombin; adjusting the pH of the solution comprising thrombin to below 7; and/or reducing the temperature of the solution comprising thrombin.

Figure 2:
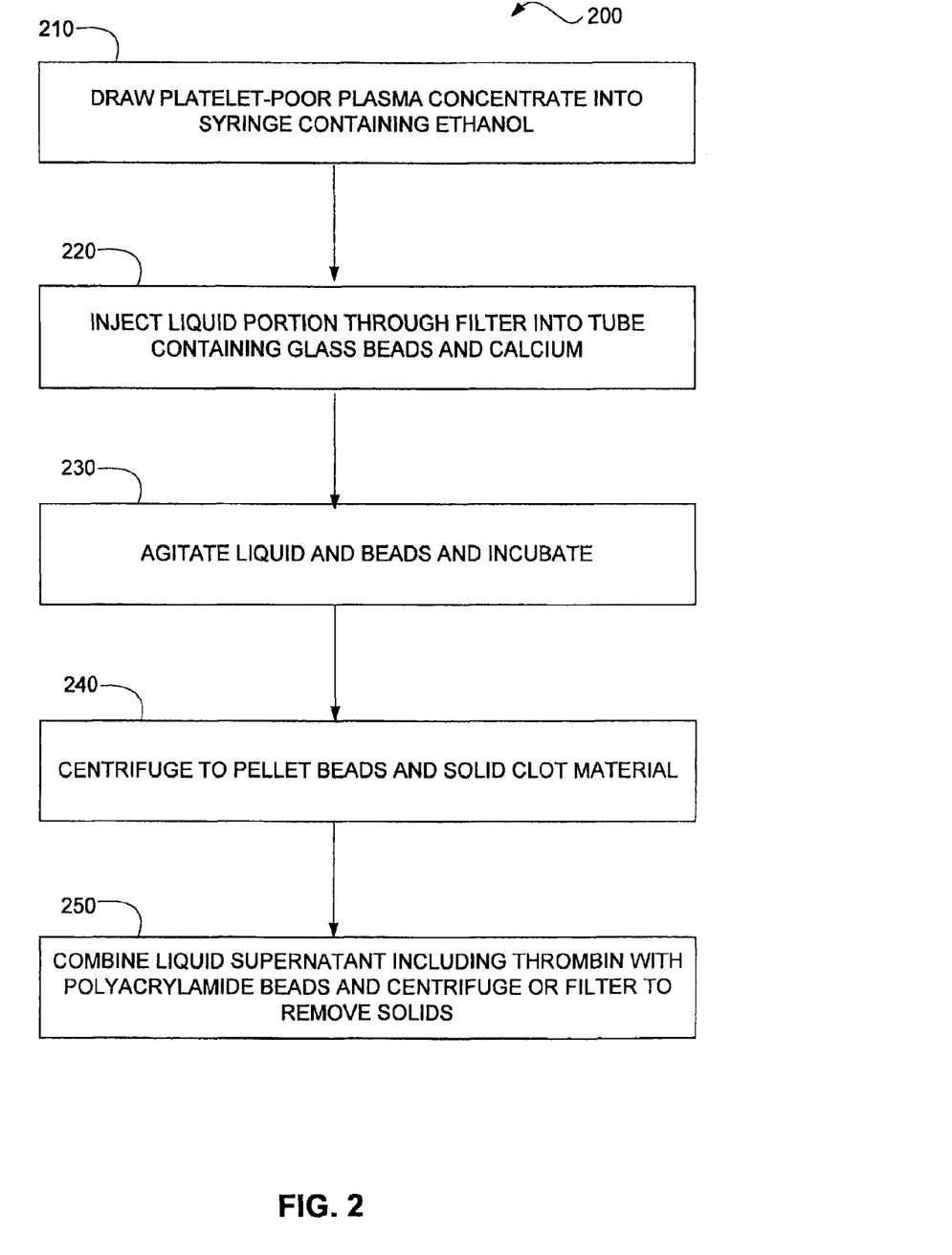
FIG. 2 is a diagrammatic illustration of another method of preparing, a solution comprising thrombin according to the present technology.

Another method 200 of preparing a solution comprising thrombin is shown in FIG. 2. At 210, platelet-poor plasma is drawn into a syringe containing ethanol in order to precipitate fibrinogen. The amount of ethanol in the syringe is proportional to the amount of platelet-poor plasma drawn into the syringe so that fibrinogen is effectively precipitated. For example, the ethanol can be about 25% of the total volume of the platelet-poor plasma. In some embodiments, the syringe can be configured to accommodate a particular amount of platelet-poor plasma while containing an amount of ethanol that corresponds to 25% of this amount. Once the fibrinogen is precipitated, the liquid is injected through a filter coupled to the syringe and into a tube. The filter traps the precipitated fibrinogen and can further trap any blood cells, platelets, and other precipitated proteins present in the liquid. Filtration results in a post-precipitation liquid.

Figure 5A:
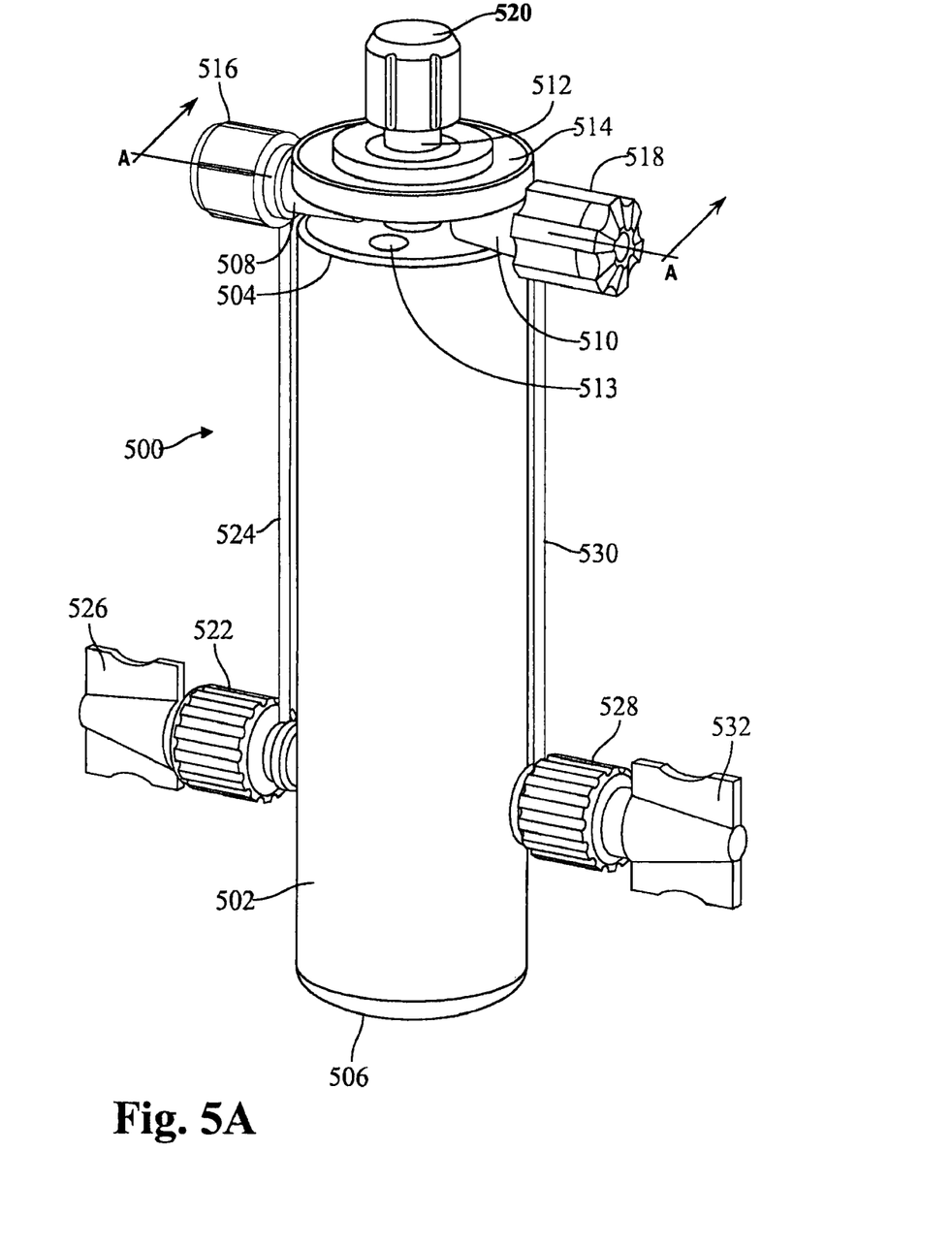
FIGS. 5A and 5B are an isometric view and a partial cross-sectional view, respectively, of a device for preparing a solution comprising thrombin according to methods of the present technology.
Figure 5B:
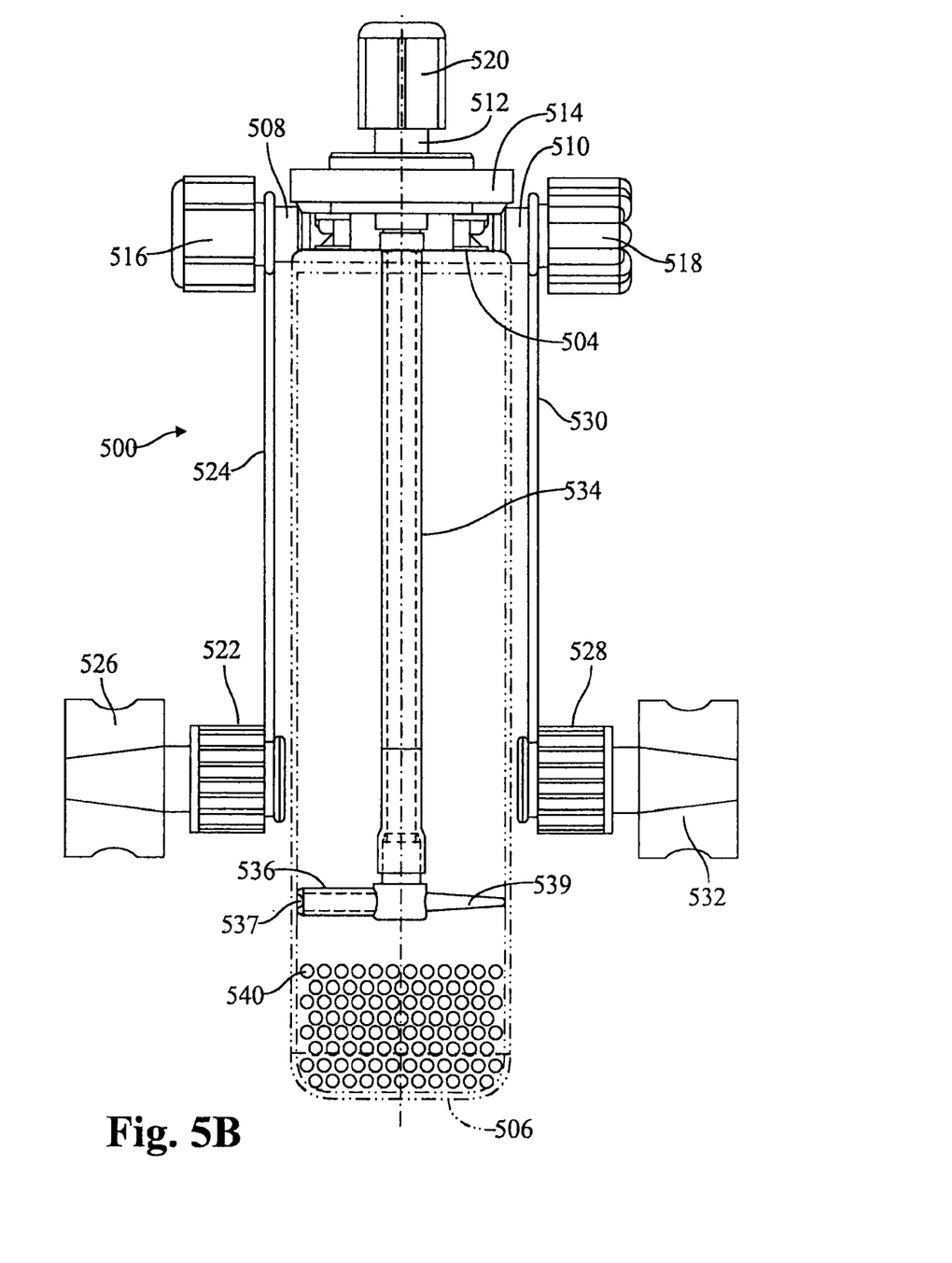

As shown at 220, the liquid is injected through the filter into a tube containing beads and calcium. The tube containing beads and calcium can be an isolation device as depicted in FIGS. 5A and 5B. The tube containing the post-precipitation liquid, beads, and calcium is then agitated and incubated as shown at 230 to form a clot. Agitation and incubation can include heating for at least about 20 minutes at a temperature of at least about 20° C. (e.g., at 37° C.). Following clot formation, the heated beads and solid clot material are pelleted by centrifugation, as indicated at 240, where the liquid supernatant including thrombin is then removed, as indicated at 250.

With reference to FIGS. 5A and 5B, the isolation device 500 generally includes a body having a cylindrical wall along with a first end 504 and a second end 506 that define a main chamber 502. At the first end 504 is a first port 508, a second port 510, a third port 512, a vent 513, and a filter 514. Each of the first port 508, the second port 510, the third port 512, and the vent 513 extend through the first end 504 and permit fluid communication between an exterior of the device 500 and the main chamber 502. The first port 508 can be covered with a first cap 516, the second port 510 can be covered with a second cap 518, and the third port 512 can be covered with a third cap 520. A first replacement cap 522 for the first port 508 can be attached to the first port 508 with a first tether 524. A first cover 526 can be secured to the first replacement cap 522 when the first replacement cap 522 is not in use. A second replacement cap 528 for the second port 510 can be attached to the second port 510 with a second tether 530. A second cover 532 can be secured to the second replacement cap 528 when the second replacement cap 528 is not in use.

The first port 508 and the second port 510 each include a stop valve to prevent materials, such as glass beads 540, from exiting the main chamber 502 through the first and the second ports 508 and 510. The valves can be any suitable valve, such as a duck-billed valve.

With particular reference to FIG. 5B, the third port 512 includes an elongated tube portion 534 that extends within the main chamber 502. The elongated portion 534 extends from the first end 504 to a depth within the main chamber 502 to permit withdrawal of select materials, such as thrombin and other blood clotting factors, from within the main chamber 502. For example and as further described below, where the main chamber 502 includes the post-precipitation liquid, glass beads, and calcium, incubation and centrifugation of this mixture forms a clotted mass including blood cells, blood plasma, and glass beads at the second end 506 of the main chamber 502. On top of the clotted mass, at the side of the clotted mass nearest the first end 504, an effluent is formed comprising thrombin and various other clotting factors. The clotted mass at the second end 506 can be visually distinguished from the effluent. In order to extract thrombin and the other clotting factors using the elongated tube portion 534, the elongated tube portion 534 extends to a depth within the main chamber 502 that is approximately level with the portion of the effluent closest to the clotted mass.

A tip 536 is provided at a distal end of the elongated portion 534. The tip 536 extends from the elongated portion 534 at about a right angle. The tip includes a recess or notch 537. Two support posts 539 extend radially from the elongated portion 534 approximately at the tip 536 to contact an interior of the main chamber 502. The support posts 539 bias the tip 536 against the interior of the main chamber 502 to retain the tip 536 at a constant position in the main chamber 502. While the tip 536 contacts the interior of the main chamber 502, the notch 537 provides an opening or clearance between the interior wall of the main chamber 502 and the tip 536 to permit the passage of material through the notch 537 and into the tip 536. The tip 536 helps to maximize the amount of materials withdrawn through the elongated portion 534, particularly when the main chamber 502 is tilted to bring additional materials surrounding the tip 536 to the notch 537. The two support posts 539 and the tip 536 help center the elongated portion 534 in the main chamber 502.

The ports 508, 510, and 512 are sized to cooperate with a suitable fluid delivery or transport device, such as a syringe. For example, the first port 508 can be sized to cooperate with a reagent syringe to permit passage of reagent through the first port 508 and into the main chamber 502; the second port 510 can be sized to cooperate with a blood syringe to permit passage of blood through the second port 510 and into the main chamber 502; and the third port 512 can be sized to cooperate with a syringe to permit withdrawal of blood components, such as thrombin and other clotting factors, from within the main chamber 502.

The filter 514 can be any suitable filter for filtering materials as they are withdrawn from within the main chamber 502 through the third port 512. The filter 514 includes a polyester screen that is mounted atop the first port 508 and the second port 510. The polyester screen includes openings that are in the range of about 15 microns to about 25 microns in size. For example, the openings can be about 17 microns in size. In place of or in addition to the filter 514, a filter similar to the filter 514 can be provided in the elongated portion 534 or at the tip 536.

The main chamber 502 further includes an activator, such as glass beads 540. The negatively charged surface of the glass beads activates clotting and the release of blood clotting factors, which form the clotted mass at the second end 506 of the main chamber 502. The glass beads 540 can be any suitable type of glass beads, such as borosilicate beads.

Methods for producing a solution comprising thrombin using the device of FIGS. 5A and 5B can include the following aspects. First, a reagent comprising calcium chloride and ethanol is injected into the main chamber 902 through the first port 908. After the reagent has been injected, the first port 508 is closed using the first replacement cap 522. Post-precipitation liquid (e.g., platelet-poor plasma where fibrinogen is precipitated and removed) is injected into the main chamber 502 through the second port 510. After the post-precipitation liquid has been injected, the second port 510 is closed using the second replacement cap 528. Optionally, the syringes and blood separation device 500 are pre-heated to a temperature of about 25° C.

The contents of the isolation device 500 are mixed by repeatedly inverting the device 500, e.g. about twelve times, so as to contact the blood with the glass beads. After mixing, the device is incubated The incubation process can be at a temperature and for a duration that will permit the contents of the device 500 to be heated at about 25° C. for about 15 minutes. Upon completion of the incubation period, a clotted mass of red blood cells, blood plasma, and glass beads forms at the second end 506 of the main chamber 502. After incubation is complete, the device 500 is shaken enough to dislodge and break-up any gel that may be present. The device 500 is then placed in a suitable centrifuge and spun at about 3200 RPM's for about 15 minutes to separate thrombin from the remaining blood components. After centrifugation, an effluent of thrombin and other clotting factors separates from the clotted mass. After centrifugation is complete, the third cap 520 is removed and a suitable extraction device, such a syringe, is used to remove the effluent of thrombin and other clotting factors from within the main chamber 502 by way of the third port 512, the elongated portion 534, and the tip 536.

Figure 3:
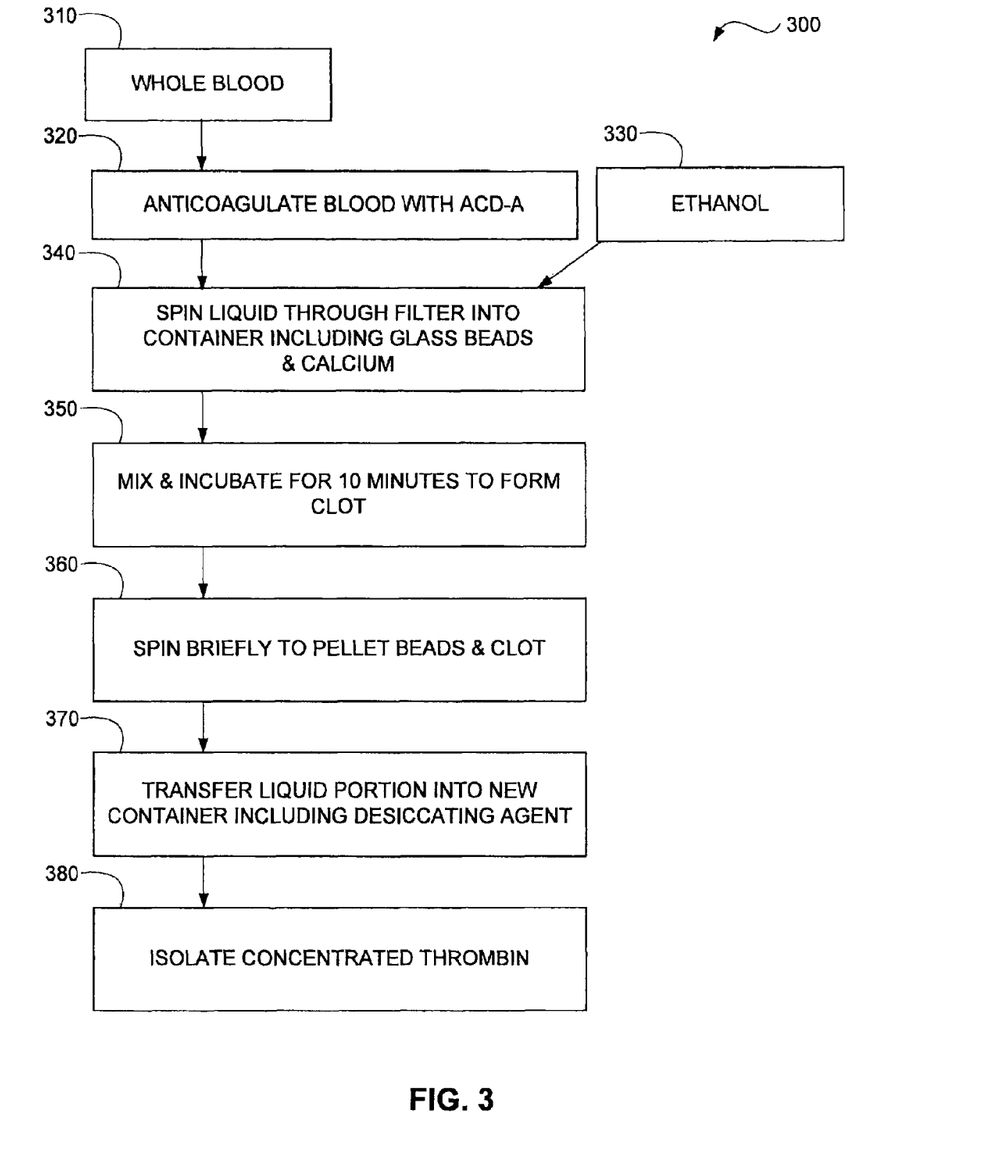
FIG. 3 is a diagrammatic illustration of another method of preparing a solution comprising thrombin according to the present technology.

Another method 300 of preparing a solution comprising thrombin is shown in FIG. 3. Whole blood 310 is drawn into a container having a volume of ACD-A to anticoagulate the blood, as shown at 320. The anticoagulated blood is then mixed with ethanol 330 to precipitate fibrinogen and the combined liquid is centrifuged through a filter to remove the precipitated fibrinogen, where the filtrate (i.e., the post-precipitation liquid) is collected in a new container including beads and calcium, as shown at 340. The post-precipitation liquid, beads, and calcium are mixed and incubated to form a clot, as shown at 350, and spun to pellet the beads and clot, as shown at 360. At 370, the liquid portion or supernatant, being a solution comprising thrombin, is then transferred into another container including a desiccating agent. The desiccating agent removes a portion of the liquid from the solution comprising thrombin. Concentrated thrombin is then isolated from the desiccating agent, as shown at 380.

The present methods can include generating thrombin for use as a tissue sealant where the thrombin can be used directly or can be further combined with other clotting factors, blood components, or blood products. For example, the solution comprising thrombin can be admixed with fibrinogen and applied to a wound, lesion, or incision as a fibrin glue. Thrombin can convert the fibrinogen into fibrin, for example in about 5 seconds to about 60 seconds, which then forms a fibrin scaffold that can seal the application site and promote healing at the site. Fibrinogen is cross-linked into a three-dimensional matrix following activation by thrombin.

In some embodiments, a method of applying a tissue sealant to a site on a subject comprises preparing a solution comprising thrombin according to the methods disclosed herein. The solution comprising thrombin is then applied to the site on the subject. For example, the solution comprising thrombin can be prepared using a liquid comprising whole blood or a blood fraction obtained from the subject, thereby providing autologous thrombin.

Methods of applying the tissue sealant can further comprise applying fibrinogen and calcium to the site on the subject. The fibrinogen and/or calcium may be combined with the thrombin or these components may be applied separately. In some cases, applying the tissue sealant comprises co-administering (i) a first solution comprising fibrinogen, and (ii) a second solution comprising thrombin and calcium. In such embodiments, the first solution and second solution are kept separate until administered so that the thrombin does not activate the fibrinogen to form a fibrin matrix until after the solutions are mixed and applied at the treatment site. The solutions may be mixed just before application to the treatment site or may be mixed at the treatment site. The thrombin, fibrinogen, and calcium can also be combined together to initiate the clotting cascade at a time prior to application to the site on the subject. As the clotting cascade progresses, a gel-like material starts to form, which can then be applied to a site for use as a tissue sealant.

The present tissue sealants and methods can be used during a surgical procedure, such as an orthopedic surgical procedure, at an incision site, an implantation site, or a repair site. The tissue sealant can assist in healing the incision in tissue by sealing the site and can further assist the body in healing thereafter.

Tissue sealants comprising thrombin prepared according to the present methods can include one or more blood components in addition to fibrinogen and calcium. Examples of blood components include whole blood, platelet-rich plasma, platelet concentrate, platelet-poor plasma or concentrates thereof. Where the blood component includes a chelating agent, such as citrate, the tissue sealant can include excess calcium to overwhelm the chelating agent and provide free calcium ions for the blood-clotting cascade.

The methods and compositions of the present technology can be used to prepare thrombin from a variety of sources, including autologous, homologous, or heterologous sources. For example, bovine thrombin can be prepared for use as a tissue sealant when performing a procedure on a human. Thrombin may also be obtained from a homologous source, such as a compatible human donor. However, it is often desirable to use autologous thrombin and autologous clotting factors (e.g., autologous fibrinogen and blood components) in the present tissue sealants to reduce the possibility of infection, immune reaction, or other side effects from using a non-autologous source. The present methods therefore can provide an autologous tissue sealant that can be prepared before or while a subject is undergoing a surgical procedure or to treat a subject presenting a lesion or trauma.

Non-Limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition or method.

The citation of references herein does not constitute an admission that those references are prior art or have any relevance to the patentability of the technology disclosed herein. Any discussion of the content of references cited in the Introduction is intended merely to provide a general summary of assertions made by the authors of the references, and does not constitute an admission as to the accuracy of the content of such references. All references cited in the "Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested. Equivalent changes, modifications and variations of some embodiments, materials, compositions and methods can be made within the scope of the present technology, with substantially similar results.

As used herein, the words "desire" or "desirable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on", "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

What is claimed is:

1. A method of preparing a solution comprising thrombin, the method comprising:
    precipitating fibrinogen from a liquid comprising platelet-poor plasma or whole blood;
    removing precipitated fibrinogen from the liquid by centrifugation or filtration to form a post-precipitation liquid;
    incubating the post-precipitation liquid with calcium and a plurality of beads to activate a portion of the post-precipitation liquid to generate a solution comprising thrombin; and
    separating the solution comprising thrombin from the beads.

2. The method of claim 1, wherein the liquid comprises platelet-poor plasma.

3. The method of claim 1, wherein the liquid comprising platelet-poor plasma or whole blood further comprises an anticoagulant.

4. The method of claim 3, wherein the anticoagulant comprises acid-citrate-dextrose solution.

5. The method of claim 1, wherein the precipitating comprises adding an organic solvent to the liquid comprising platelet-poor plasma or whole blood.

6. The method of claim 5, wherein the organic solvent is methanol, ethanol, acetone, or combinations thereof.

7. The method of claim 1, wherein the incubating comprises incubating for about 5 to about 10 minutes.

8. The method of claim 1, wherein the liquid comprising platelet-poor plasma or whole blood further comprises a chelator and the calcium is present in an amount greater than an amount that can be complexed by the chelator.

9. The method of claim 1, wherein the beads are glass beads, polystyrene beads, or combinations thereof.

10. The method of claim 1, wherein separating the solution comprising thrombin from the beads comprises centrifuging the beads and post-precipitation liquid and removing a portion of the post-precipitation liquid supernatant as the solution comprising thrombin.

11. The method of claim 1, further comprising at least one of: adding glycerin, a polyol, or alcohol to the solution comprising thrombin; adding a chelator to complex calcium in the solution comprising thrombin; adjusting the pH of the solution comprising thrombin to below 7; and reducing the temperature of the solution comprising thrombin.

12. The method of claim 1, wherein:
precipitating fibrinogen from a liquid comprising platelet-poor plasma or whole blood comprises adding ethanol to platelet-poor plasma;
removing precipitated fibrinogen from the liquid to form a post-precipitation liquid comprises filtering the liquid;
incubating the post-precipitation liquid with calcium and a plurality of beads to activate a portion of the post-precipitation liquid to generate a solution comprising thrombin comprises mixing the post-precipitation liquid, calcium chloride, and beads; and
separating the solution comprising thrombin from the beads comprises centrifuging the beads and post-precipitation liquid and removing a portion of the post-precipitation liquid supernatant as the solution comprising thrombin.

13. The method of claim 1, wherein
precipitating fibrinogen from a liquid comprising platelet-poor plasma or whole blood comprises drawing platelet-poor plasma or whole blood into a syringe containing ethanol, wherein the syringe further contains an anticoagulant when the liquid comprises whole blood;
removing precipitated fibrinogen from the liquid to form a post-precipitation liquid comprises coupling a filter to the syringe and filtering the liquid into a tube comprising the calcium and the plurality of beads;
incubating the post-precipitation liquid with calcium and a plurality of beads to activate a portion of the post-precipitation liquid to generate a solution comprising thrombin comprises mixing the post-precipitation liquid, calcium chloride, and beads in the tube; and
separating the solution comprising thrombin from the beads comprises centrifuging the beads and post-precipitation liquid and removing a portion of the post-precipitation liquid supernatant as the solution comprising thrombin.

14. The method of claim 13, further comprising concentrating the solution comprising thrombin.

15. The method of claim 14, wherein the beads are polyacrylamide beads, and wherein concentrating the solution comprising thrombin comprises incubating the solution with polyacrylamide beads.

16. The method of claim 1, further comprising:
applying the solution comprising thrombin to a site on a subject.

17. The method of claim 16, wherein the solution comprising thrombin is prepared from platelet-rich plasma or whole blood obtained from the subject.

18. A method of preparing a solution comprising thrombin from a whole blood sample in a container having a mixing assembly, the method comprising:
collecting a whole blood sample;
precipitating fibrinogen in the whole blood sample;
removing precipitated fibrinogen from the whole blood sample to form a post-precipitation whole blood sample, by filtering the whole blood sample or centrifuging the whole blood sample to sediment precipitated fibrinogen;
introducing the post-precipitation whole blood sample into the container;
mixing the post-precipitation whole blood sample with a calcium salt and with activating beads; and
withdrawing a volume of a solution comprising thrombin from the container after mixing the post-precipitation whole blood sample with the calcium salt and activating beads.

19. The method of claim 18, wherein the precipitating comprises adding an organic solvent selected from the group consisting of methanol, ethanol, acetone, and combinations thereof.

20. The method of claim 18, further comprising admixing ethanol to the mixed post-precipitation whole blood sample to achieve a concentration of about 4 percent (vol.) to about 7 percent (vol.) ethanol in the mixed post-precipitation whole blood sample.

21. The method of claim 18, wherein the post-precipitation whole blood sample is mixed with polyacrylamide beads.

22. The method of claim 18, further comprising:
applying the solution comprising thrombin to a site on a subject.

23. The method of claim 22, wherein the solution comprising thrombin is prepared from a whole blood sample collected from the subject.

* * * * *